United States Patent
Kroeger et al.

(10) Patent No.: US 11,382,632 B2
(45) Date of Patent: Jul. 12, 2022

(54) VASCULAR OCCLUSION DEVICE

(71) Applicant: BOSTON SCIENTIFIC SCIMED, INC., Maple Grove, MN (US)

(72) Inventors: John D. Kroeger, Mounds View, MN (US); David Robert Wulfman, Minneapolis, MN (US); Hoi Ki Ricky Chow, New Brighton, MN (US); Adeniyi O. Aremu, Brooklyn Park, MN (US); Timothy A. Ostroot, Cokato, MN (US); Nicholas Lee Tassoni, Andover, MN (US); Daniel K. Tomaschko, Savage, MN (US); David Pettijohn, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 133 days.

(21) Appl. No.: 16/454,698

(22) Filed: Jun. 27, 2019

(65) Prior Publication Data

US 2020/0000476 A1  Jan. 2, 2020

Related U.S. Application Data

(60) Provisional application No. 62/690,582, filed on Jun. 27, 2018.

(51) Int. Cl.
*A61B 17/12* (2006.01)

(52) U.S. Cl.
CPC .. *A61B 17/12109* (2013.01); *A61B 17/12031* (2013.01); *A61B 17/12168* (2013.01)

(58) Field of Classification Search
CPC ........ A61B 17/12109; A61B 17/12168; A61B 17/12031; A61B 17/1215; A61B 17/12145; A61B 17/12036; A61B 17/12022; A61B 17/12; A61B 17/1204; A61B 17/12045; A61B 17/12113; A61B 17/12118; A61B 17/1214; A61B 17/12172; A61B 17/12177; A61B 2017/12127; A61F 2/958; A61F 2/86; A61M 25/10; A61M 2025/1054
See application file for complete search history.

(56) References Cited

U.S. PATENT DOCUMENTS

| | | | |
|---|---|---|---|
| 6,361,545 B1 * | 3/2002 | Macoviak | A61B 17/221 606/151 |
| 6,569,145 B1 * | 5/2003 | Shmulewitz | A61B 17/12022 604/102.01 |
| 7,811,300 B2 | 10/2010 | Feller, III et al. | |
| 8,025,495 B2 | 9/2011 | Hadert et al. | |
| 8,968,352 B2 | 3/2015 | Teoh et al. | |
| 9,168,043 B2 | 10/2015 | van der Burg et al. | |

(Continued)

*Primary Examiner* — Diane D Yabut
*Assistant Examiner* — Christina C Lauer
(74) *Attorney, Agent, or Firm* — Seager, Tufte & Wickhem LLP

(57) ABSTRACT

A vascular occlusion device for deployment within a lumen of a vessel may include a self-expanding frame configured to shift between a collapsed configuration and an expanded configuration, the self-expanding frame defining a perimeter of an interior space disposed within the self-expanding frame, and an occlusive membrane secured to the self-expanding frame. The occlusive membrane may include a suspended portion disposed within the self-expanding frame and spaced apart from the perimeter of the interior space.

19 Claims, 8 Drawing Sheets

(56) References Cited

U.S. PATENT DOCUMENTS

| | | |
|---|---|---|
| 2004/0143288 A1 | 7/2004 | Searle |
| 2005/0055082 A1* | 3/2005 | Ben Muvhar ............ A61F 2/848 623/1.15 |
| 2006/0173490 A1* | 8/2006 | Lafontaine .............. A61F 2/013 606/200 |
| 2014/0277096 A1* | 9/2014 | Richter ............ A61B 17/12131 606/200 |
| 2014/0371778 A1 | 12/2014 | Rudakov et al. |
| 2016/0310147 A1 | 10/2016 | Squire et al. |
| 2017/0007260 A1* | 1/2017 | O'Brien ............ A61B 17/12145 |
| 2017/0354421 A1* | 12/2017 | Maguire ............ A61B 17/1214 |
| 2017/0367710 A1 | 12/2017 | Yang |

\* cited by examiner

VASCULAR OCCLUSION DEVICE

CROSS-REFERENCE TO RELATED APPLICATIONS

This application claims the benefit of priority under 35 U.S.C. § 119 to U.S. Provisional Application Ser. No. 62/690,582, filed Jun. 27, 2018, the entirety of which is incorporated herein by reference.

TECHNICAL FIELD

The present disclosure pertains to medical devices and methods for manufacturing and/or using occlusive medical devices. More particularly, the present disclosure pertains to a vascular occlusion device.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a vascular occlusion device for deployment within a lumen of a vessel may comprise a self-expanding frame configured to shift between a collapsed configuration and an expanded configuration, the self-expanding frame defining a perimeter of an interior space disposed within the self-expanding frame; and an occlusive membrane secured to the self-expanding frame. The occlusive membrane may include a suspended portion disposed within the self-expanding frame and spaced apart from the perimeter of the interior space.

In addition or alternatively, and in a second aspect, the self-expanding frame is configured to exert a radially outward force against an interior wall of the vessel in the expanded configuration.

In addition or alternatively, and in a third aspect, the occlusive membrane includes an anchoring portion configured to exert an additive radially outward force against the interior wall of the vessel when fluid flows into the occlusive membrane in the expanded configuration.

In addition or alternatively, and in a fourth aspect, the anchoring portion is attached to the self-expanding frame.

In addition or alternatively, and in a fifth aspect, the self-expanding frame is embedded within the anchoring portion.

In addition or alternatively, and in a sixth aspect, the anchoring portion defines a length measured along a central longitudinal axis of self-expanding frame, the suspended portion defines a length measured along the central longitudinal axis, and the length of the suspended portion is greater than the length of the anchoring portion.

In addition or alternatively, and in a seventh aspect, the occlusive membrane includes a distal end attached to a distal hub of the self-expanding frame.

In addition or alternatively, and in an eighth aspect, the suspended portion of the occlusive membrane tapers radially inward toward a distal hub of the self-expanding frame.

In addition or alternatively, and in a ninth aspect, the occlusive membrane includes an open end oriented towards a proximal hub of the self-expanding frame and a closed end oriented towards a distal hub of the self-expanding frame.

In addition or alternatively, and in a tenth aspect, the vascular occlusion device may further include at least one vent proximate the closed end of the occlusive membrane.

In addition or alternatively, and in an eleventh aspect, the at least one vent includes a plurality of cuts through the occlusive membrane, the plurality of cuts being configured to permit the at least one vent to open at a pre-defined pressure level.

In addition or alternatively, and in a twelfth aspect, the vascular occlusion device may further include at least one vent formed within the suspended portion of the occlusive membrane proximal of the closed end.

In addition or alternatively, and in a thirteenth aspect, a vascular occlusion device for deployment within a lumen of a vessel, comprising a self-expanding frame configured to shift between a collapsed configuration and an expanded configuration, wherein the self-expanding frame is configured to exert a radially outward force against an interior wall of the vessel in the expanded configuration, and an occlusive membrane having an open end and a closed end, the occlusive membrane being secured to the self-expanding frame. At least a portion of the occlusive membrane may be configured to exert an additive radially outward force against the interior wall of the vessel when fluid flows into the open end of the occlusive membrane in the expanded configuration. At least a portion of the self-expanding frame extending from the open end of the occlusive membrane toward the closed end of the occlusive membrane, may be embedded within the occlusive membrane. At least one vent may be formed within one or more struts of the self-expanding frame.

In addition or alternatively, and in a fourteenth aspect, the at least one vent is formed within the self-expanding frame at a location radially inward of a maximum outer extent of the self-expanding frame.

In addition or alternatively, and in a fifteenth aspect, each of the at least one vent may be disposed at a node within a body of the self-expanding frame.

In addition or alternatively, and in a sixteenth aspect, a vascular occlusion device for deployment within a lumen of a vessel, comprising a self-expanding frame configured to shift between a collapsed configuration and an expanded configuration, the self-expanding frame defining a perimeter of an interior space disposed within the self-expanding frame, and an occlusive membrane secured to the self-expanding frame. The occlusive membrane may include a suspended portion disposed within the self-expanding frame and spaced apart from the perimeter of the interior space. The self-expanding frame may be configured to exert a radially outward force against an interior wall of the vessel in the expanded configuration. The suspended portion may include a proximal suspended portion opening toward a proximal hub of the self-expanding frame and a distal suspended portion opening toward a distal hub of the self-expanding frame, the proximal suspended portion and the distal suspended portion being joined together at a narrowed waist of the occlusive membrane.

In addition or alternatively, and in a seventeenth aspect, the proximal suspended portion includes a proximal anchoring portion configured to exert an additive radially outward force against the interior wall of the vessel when fluid flows into the occlusive membrane in a distal direction in the expanded configuration.

In addition or alternatively, and in an eighteenth aspect, the proximal anchoring portion is attached to the self-expanding frame.

In addition or alternatively, and in a nineteenth aspect, the distal suspended portion includes a distal anchoring portion configured to exert an additive radially outward force against the interior wall of the vessel when fluid flows into the occlusive membrane in a proximal direction in the expanded configuration.

In addition or alternatively, and in a twentieth aspect, the distal anchoring portion is attached to the self-expanding frame.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
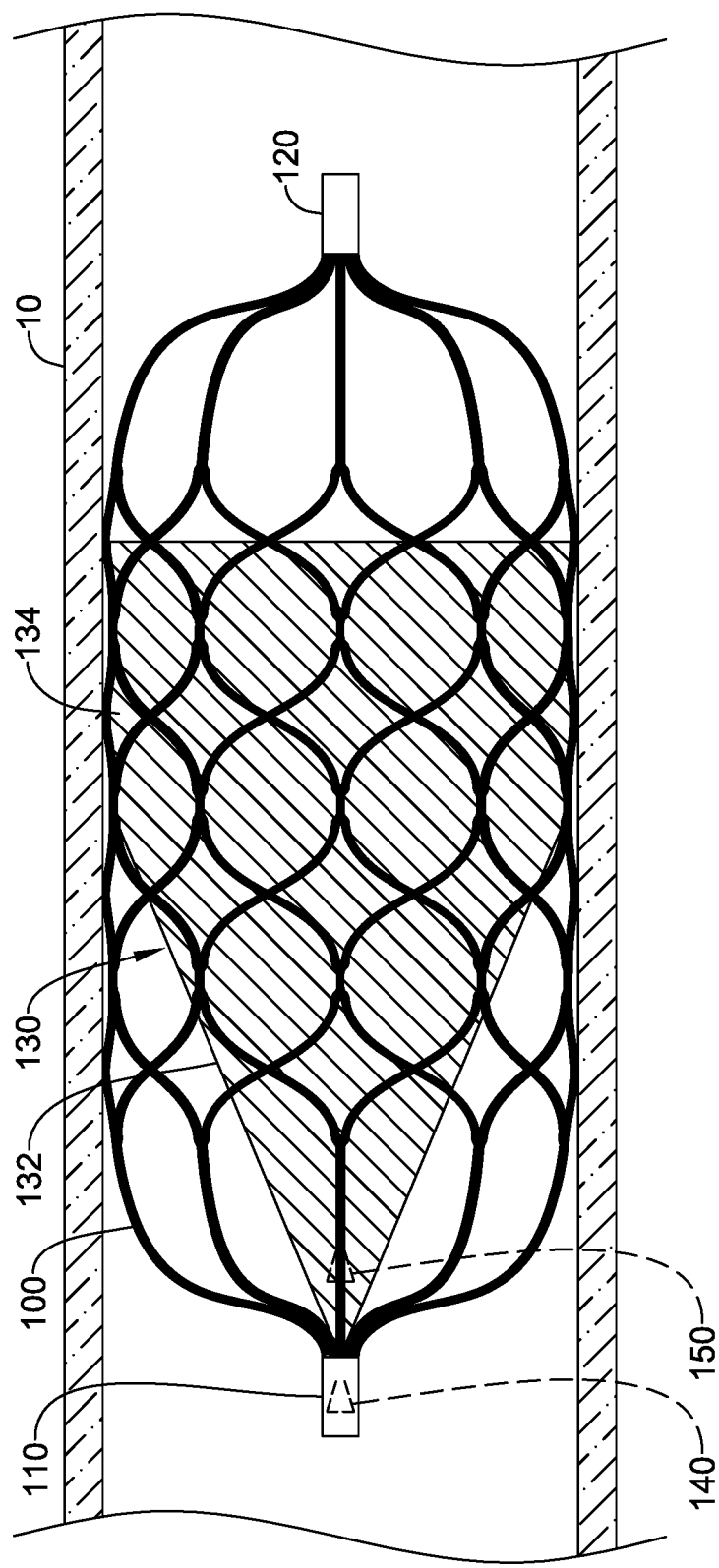
FIG. 1 illustrates aspects of an example vascular occlusion device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions, and methods of making such devices. The devices and methods disclosed herein may also provide a number of additional desirable features and benefits as described in more detail below.

In some embodiments, an example vascular occlusion device for deployment within a lumen of a vessel 10 may comprise a self-expanding frame 100, as seen in FIGS. 1-8. For example, the self-expanding frame may be made from a shape memory material, may be heat set to a predetermined configuration, or may have other characteristics capable of influencing its behavior. In some embodiments, the self-expanding frame 100 may be mechanically expandable or balloon expandable. Other configurations are also contemplated. The self-expanding frame 100 may include a distal hub 110 disposed at a distal end of the self-expanding frame 100 and a proximal hub 120 disposed at a proximal end of the self-expanding frame 100.

The self-expanding frame 100 may include a body formed from a plurality of interconnected struts and/or a lattice support structure. For example, in some embodiments, the body of the self-expanding frame 100 may have the form and/or appearance of an expandable stent. In some embodiments, the self-expanding frame 100 and/or the body of the self-expanding frame 100 may include a plurality of closed cells forming a series of adjacent rows of cells along a length of the self-expanding frame 100 and/or the body of the self-expanding frame 100. The self-expanding frame 100 may define a perimeter of an interior space disposed within the self-expanding frame 100.

The self-expanding frame 100 may be configured to shift between a collapsed configuration and an expanded configuration upon delivery to a treatment site within the vessel 10. In the expanded configuration, the body of the self-expanding frame 100 and/or the plurality of closed cells forming the series of adjacent rows of cells may be "open" or enlarged compared to the collapsed configuration. In the expanded configuration, the body of the self-expanding frame 100 and/or the plurality of closed cells forming the series of adjacent rows of cells may define an outer diameter and/or outer extent greater than the outer diameter or outer extent of the body of the self-expanding frame 100 and/or the plurality of closed cells forming the series of adjacent rows of cells in the collapsed configuration. In some embodiments, the self-expanding frame 100 may be configured to exert a radially outward force against an interior wall of the vessel 10 in the expanded configuration and/or as the self-expanding frame 100 approaches or is shifting toward the expanded configuration. The radially outward force against the interior wall of the vessel 10 may be configured to anchor the vascular occlusion device and/or the self-expanding frame 100 at the treatment site, so as to prevent migration of the vascular occlusion device and/or the self-expanding frame 100 downstream within the lumen of the vessel 10.

In some embodiments, the distal hub 110 may be integrally formed and/or unitary with the body of the self-expanding frame 100 at the distal end of the self-expanding frame 100. In some embodiments, the self-expanding frame 100 may include a first plurality of longitudinally-oriented struts extending away from and/or distally from the body of the self-expanding frame 100 and/or the plurality of closed cells forming the series of adjacent rows of cells toward and/or to the distal hub 110. In some embodiments, the self-expanding frame 100 may include a second plurality of longitudinally-oriented struts extending in a proximal direction from the body of the self-expanding frame 100 and/or the plurality of closed cells forming the series of adjacent rows of cells toward and/or to the proximal hub 120. In some embodiments, the proximal hub 120 may be integrally formed and/or unitary with the body of the self-expanding frame 100.

In some embodiments, a method of making the vascular occlusion device and/or the self-expanding frame 100 may include cutting a tubular member, a catheter, a hypotube, or other similar tubular structure to form the self-expanding frame 100. In some embodiments, the self-expanding frame 100 may be formed and/or cut from a flat sheet of material that is subsequently rolled to form a tubular member or tubular structure and welded, bonded, or otherwise joined along a seam and/or a joint formed by edges of the flat sheet of material brought together. In some embodiments, the self-expanding frame 100 may be laser cut from the tubular member, the catheter, the hypotube, or other similar tubular structure and/or the flat sheet of material. Some suitable but non-limiting materials for the self-expanding frame 100, the distal hub 110, and/or the proximal hub 120, for example metallic materials, polymer materials, composite materials, shape memory materials, etc., are described below.

In some embodiments, the method may include heat-setting the self-expanding frame 100, the body of the self-expanding frame 100, the plurality of closed cells forming the series of adjacent rows of cells, and/or the first plurality of longitudinally-oriented struts to define the expanded configuration of the self-expanding frame 100 and/or the body of the self-expanding frame 100. In some embodiments, the method may include heat-setting the self-expanding frame 100, the body of the self-expanding frame 100, the plurality of closed cells forming the series of adjacent rows of cells, and/or the first plurality of longitudinally-oriented struts to define the expanded configuration of the self-expanding frame 100 and/or the body of the self-expanding frame 100 with a mandrel in place and/or disposed within the self-expanding frame 100. Other methods and/or means of heat-setting the self-expanding frame 100 and/or defining the collapsed configuration and the expanded configuration of the self-expanding frame 100 are also contemplated.

FIG. 1 illustrates an example vascular occlusion device comprising the self-expanding frame 100 and an occlusive membrane 130 secured to the self-expanding frame 100. The occlusive membrane 130 may be substantially impermeable to fluid such that the occlusive membrane 130 is configured to substantially occlude and/or stop fluid flow through the lumen of the vessel 10. In some embodiments, the occlusive membrane 130 may be configured to completely occlude and/or stop fluid flow through the lumen of the vessel 10, initially and/or over time. Some suitable but non-limiting materials for the occlusive membrane 130, for example metallic materials, polymer materials, composite materials, etc., are described below.

In some embodiments, the occlusive membrane 130 may include a suspended portion 132 disposed within the self-expanding frame 100 and spaced apart from the perimeter of the interior space disposed within the self-expanding frame 100. In some embodiments, the occlusive membrane 130 may include an anchoring portion 134 configured to exert an additive radially outward force against the interior wall of the vessel 10 when fluid flows into the occlusive membrane 130 in the expanded configuration. In some embodiments, the anchoring portion 134 of the occlusive membrane 130 may be attached to the self-expanding frame 100, for example the occlusive membrane 130 may be attached to the body of the self-expanding frame 100. In at least some embodiments, at least a portion of the self-expanding frame 100 may be embedded within and/or disposed between adjacent layers of the anchoring portion 134 of the occlusive membrane 130. For example, a portion of the body of the self-expanding frame 100 may be embedded within and/or disposed between adjacent layers of the anchoring portion 134 of the occlusive membrane 130. Other configurations are also contemplated.

In some embodiments, the anchoring portion 134 of the occlusive membrane 130 may define a length measured along a central longitudinal axis of the self-expanding frame 100. In some embodiments, the suspended portion 132 of the occlusive membrane 130 may define a length measured along the central longitudinal axis of the self-expanding frame 100. In at least some embodiments, the length of the suspended portion 132 may be greater than the length of the anchoring portion 134. In some embodiments, the length of the suspended portion 132 may be substantially equal to the length of the anchoring portion 134. In some embodiments, the length of the suspended portion 132 may be less than the length of the anchoring portion 134. The length of the suspended portion 132 relative to the length of the anchoring portion 134 may be changed or adjusted depending on how much additive radially outward force is desired in a given application or use.

In some embodiments, the occlusive membrane 130 may include a distal end attached to the distal hub 110 of the self-expanding frame 100. In some embodiments, the suspended portion 132 of the occlusive membrane 130 may taper radially inward from the anchoring portion 134 toward the distal hub 110 of the self-expanding frame 100. In some embodiments, the occlusive membrane 130 may include an open end near and/or oriented towards the proximal hub 120 of the self-expanding frame 100 and a closed end near and/or oriented towards the distal hub 110 of the self-expanding frame 100. Other configurations are also contemplated.

As fluid flows into the open end of the occlusive membrane 130, the occlusive membrane 130 may expand radially outward and/or may occlude the lumen of the vessel 10. In some instances, vessel occlusion may take place slowly over time. As time passes following vessel occlusion, thrombus formation and/or tissue overgrowth on and/or around the occlusive membrane 130 may take place, further occluding and/or sealing off the lumen of the vessel 10. In some instances, vessel occlusion may occur very quickly and/or immediately. However, in some cases, immediate occlusion may cause in vessel flexing and/or expansion due to vessel spasm. In some cases, pressure increases following immediate occlusion may exceed anchoring forces and cause or allow the vascular occlusion device to move and/or shift downstream within the lumen of the vessel 10. Additionally, it may be desirable for the vascular occlusion device to be recapturable and/or repositionable. However, the occlusive membrane 130 may trap and/or hold fluid during a recapture step resulting in high recapture forces as the fluid is unable to vent and/or exit the vascular occlusion device and/or the occlusive membrane 130. Some possible solutions to the above-referenced conditions may involve a modification to the vascular occlusion device.

Figure 2:
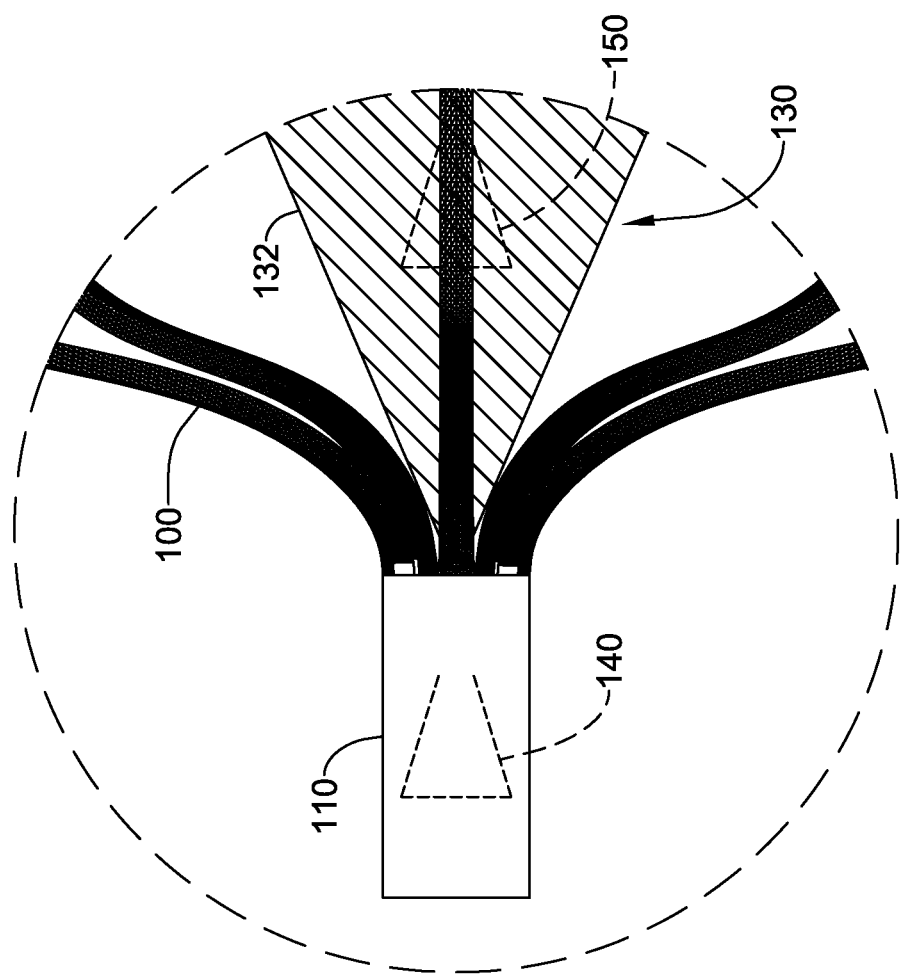
FIG. 2 is a detailed view illustrating aspects of an example vascular occlusion device.

In some embodiments, the vascular occlusion device may include at least one vent 140/150 proximate the closed end of the occlusive membrane 130, as shown in FIGS. 1 and 2. In some embodiments, the at least one vent 140 may be formed within the distal hub 110 of the self-expanding frame 100. In some embodiments, the at least one vent 140 may include a plurality of cuts through the distal hub 110, the plurality of cuts being configured to permit the at least one vent 140 to open at a pre-defined pressure level. In one example, the plurality of cuts may form a flap configured to assume a normally closed position at a fluid pressure within the occlusive membrane 130 less than the pre-defined pressure level. Upon reaching and/or surpassing the pre-defined pressure level within the occlusive membrane 130, the flap may be configured to assume an open position thereby permitting fluid to pass through the at least one vent to relieve pressure as thrombus and/or tissue overgrowth forms on and/or around the occlusive membrane 130 and/or the at least one vent 140.

In some embodiments, the at least one vent 150 may be formed within the suspended portion 132 of the occlusive membrane 130 proximal of the closed end of the occlusive membrane 130. In some embodiments, the at least one vent 150 may include a plurality of cuts through the occlusive membrane 130, the plurality of cuts being configured to permit the at least one vent 150 to open at a pre-defined pressure level. In one example, the plurality of cuts may form a flap configured to assume a normally closed position at a fluid pressure within the occlusive membrane 130 less than the pre-defined pressure level. Upon reaching and/or surpassing the pre-defined pressure level within the occlusive membrane 130, the flap may be configured to assume an open position thereby permitting fluid to pass through the at least one vent 150 to relieve pressure as thrombus and/or tissue overgrowth forms on and/or around the occlusive membrane 130 and/or the at least one vent 150.

Figure 3:
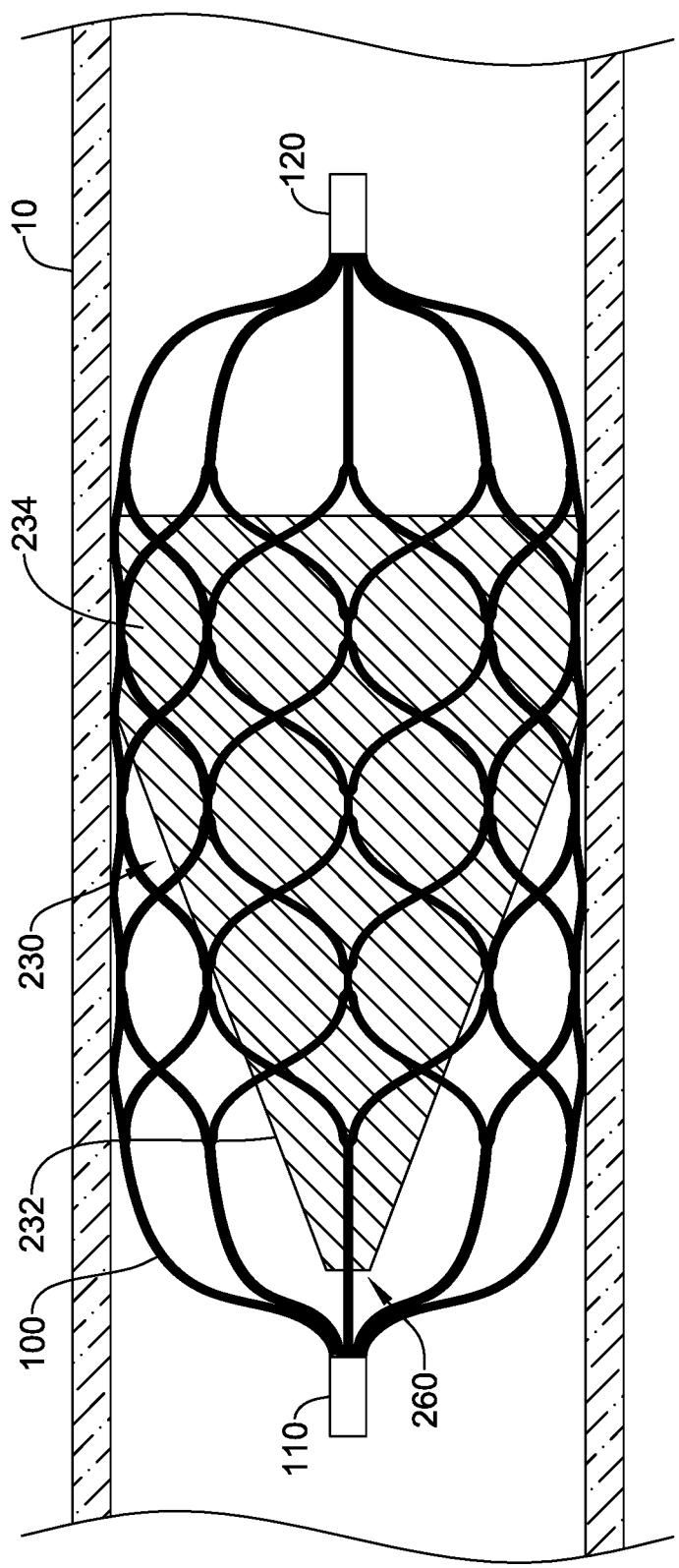
FIG. 3 illustrates aspects of an example vascular occlusion device.

In an alternative example illustrated in FIG. 3, in some embodiments, the vascular occlusion device may comprise the self-expanding frame 100 and an occlusive membrane 230 secured to the self-expanding frame 100. The occlusive membrane 230 may be substantially impermeable to fluid such that the occlusive membrane 230 is configured to substantially occlude and/or stop fluid flow through the lumen of the vessel 10. In some embodiments, the occlusive membrane 230 may be configured to completely occlude and/or stop fluid flow through the lumen of the vessel 10, initially and/or over time. Some suitable but non-limiting materials for the occlusive membrane 230, for example metallic materials, polymer materials, composite materials, etc., are described below.

In some embodiments, the occlusive membrane 230 may include a suspended portion 232 disposed within the self-expanding frame 100 and spaced apart from the perimeter of the interior space disposed within the self-expanding frame 100. In some embodiments, the occlusive membrane 230 may include an anchoring portion 234 configured to exert an additive radially outward force against the interior wall of the vessel 10 when fluid flows into the occlusive membrane 230 in the expanded configuration. In some embodiments, the anchoring portion 234 of the occlusive membrane 230 may be attached to the self-expanding frame 100, for example the occlusive membrane 230 may be attached to the body of the self-expanding frame 100. In at least some embodiments, at least a portion of the self-expanding frame 100 may be embedded within and/or disposed between adjacent layers of the anchoring portion 234 of the occlusive membrane 230. For example, a portion of the body of the self-expanding frame 100 may be embedded within and/or disposed between adjacent layers of the anchoring portion 234 of the occlusive membrane 230. Other configurations are also contemplated.

In some embodiments, the anchoring portion 234 of the occlusive membrane 230 may define a length measured along a central longitudinal axis of the self-expanding frame 100. In some embodiments, the suspended portion 232 of the occlusive membrane 230 may define a length measured along the central longitudinal axis of the self-expanding frame 100. In at least some embodiments, the length of the suspended portion 232 may be greater than the length of the anchoring portion 234. In some embodiments, the length of the suspended portion 232 may be substantially equal to the length of the anchoring portion 234. In some embodiments, the length of the suspended portion 232 may be less than the length of the anchoring portion 234. The length of the suspended portion 232 relative to the length of the anchoring portion 234 may be changed or adjusted depending on how much additive radially outward force is desired in a given application or use.

In some embodiments, the occlusive membrane 230 may include a distal end spaced proximally from the distal hub 110 of the self-expanding frame 100. In some embodiments, the suspended portion 232 of the occlusive membrane 230 may taper radially inward from the anchoring portion 234 toward the distal hub 110 of the self-expanding frame 100. In some embodiments, the occlusive membrane 230 may include an open end near and/or oriented towards the proximal hub 120 of the self-expanding frame 100 and a closed end near and/or oriented towards the distal hub 110 of the self-expanding frame 100. Other configurations are also contemplated.

In some embodiments, the vascular occlusion device may include at least one vent 260 proximate the closed end of the occlusive membrane 230, as shown in FIG. 3. In some embodiments, the at least one vent 260 may be formed at the closed end of the occlusive membrane 230 as an opening or aperture. In some embodiments, the distal end and/or the closed end may be trimmed off to form the at least one vent 260, the at least one vent 260 being configured to permit fluid to slowly pass through the at least one vent 260 to relieve pressure as thrombus and/or tissue overgrowth forms on and/or around the occlusive membrane 230 and/or the at least one vent 260.

Figure 4:
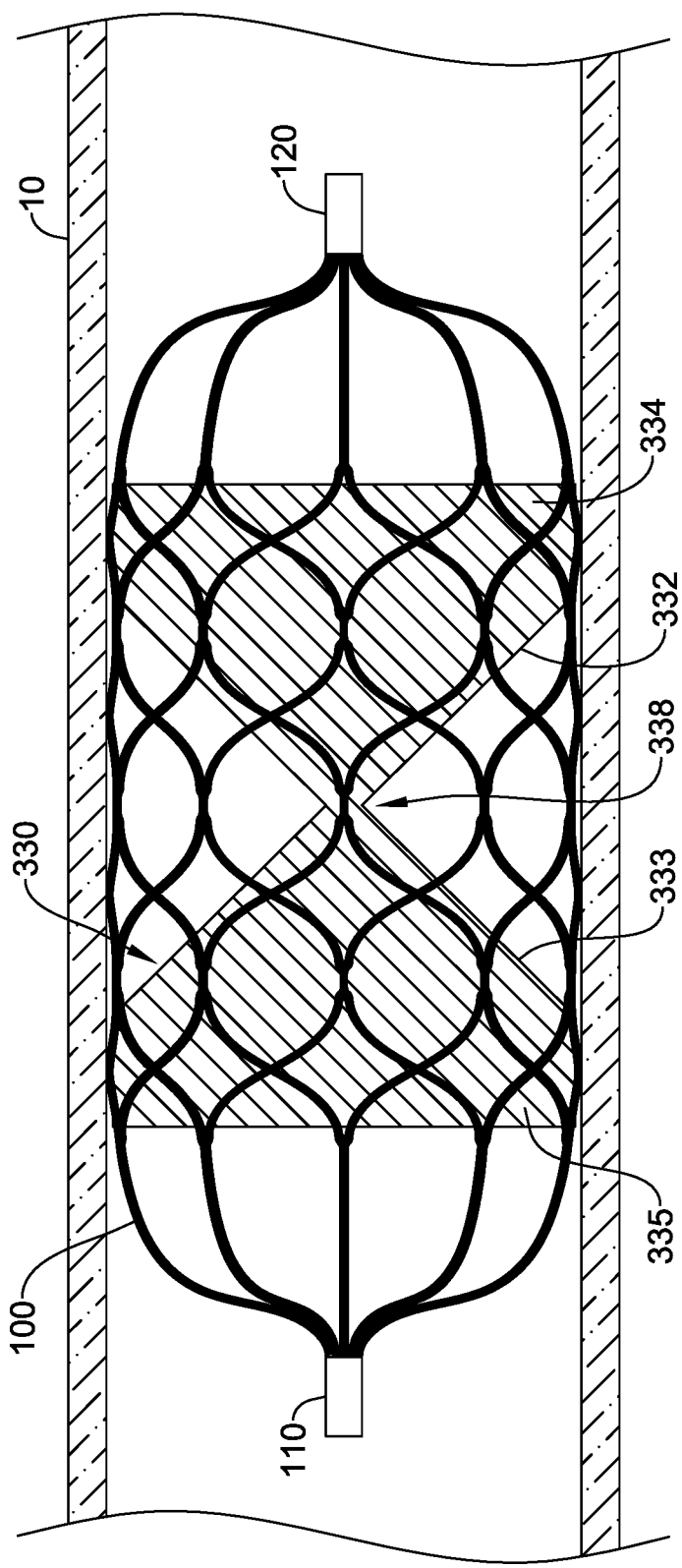
FIG. 4 illustrates aspects of an example vascular occlusion device.

In an alternative example illustrated in FIG. 4, in some embodiments, the vascular occlusion device may comprise the self-expanding frame 100 and an occlusive membrane 330 secured to the self-expanding frame 100. The occlusive membrane 330 may be substantially impermeable to fluid such that the occlusive membrane 330 is configured to substantially occlude and/or stop fluid flow through the lumen of the vessel 10. In some embodiments, the occlusive membrane 330 may be configured to completely occlude and/or stop fluid flow through the lumen of the vessel 10, initially and/or over time. Some suitable but non-limiting materials for the occlusive membrane 330, for example metallic materials, polymer materials, composite materials, etc., are described below.

In some embodiments, the occlusive membrane 330 may include a suspended portion disposed within the self-expanding frame 100 and spaced apart from the perimeter of the interior space disposed within the self-expanding frame 100. In some embodiments, the suspended portion may include a proximal suspended portion 332 opening toward the proximal hub 120 of the self-expanding frame 100 and a distal suspended portion 333 opening toward the distal hub 110 of the self-expanding frame 100. In at least some embodiments, the proximal suspended portion 332 and the distal suspended portion 333 may be joined together at a narrowed waist 338 of the occlusive membrane 330, proximate a center of the vascular occlusion device and/or the body of the self-expanding frame 100.

In some embodiments, the proximal suspended portion 332 of the occlusive membrane 330 may include a proximal anchoring portion 334 configured to exert an additive radially outward force against the interior wall of the vessel 10 when fluid flows into the occlusive membrane 330 in a distal direction in the expanded configuration. In some embodiments, the distal suspended portion 333 of the occlusive membrane 330 may include a distal anchoring portion 335 configured to exert an additive radially outward force against the interior wall of the vessel 10 when fluid flows into the occlusive membrane 330 in a proximal direction in the expanded configuration. Accordingly, the vascular occlusion device having the occlusive membrane 330 may be configured for bi-directional use, wherein direction of approach to the treatment site does not matter for placement of the vascular occlusion device.

In some embodiments, the proximal anchoring portion 334 of the occlusive membrane 330 may be attached to the self-expanding frame 100, for example the proximal anchoring portion 334 of the occlusive membrane 330 may be attached to a proximal portion of the body of the self-expanding frame 100. In at least some embodiments, at least a portion of the self-expanding frame 100 may be embedded within and/or disposed between adjacent layers of the proximal anchoring portion 334 of the occlusive membrane 330. For example, a portion of the body of the self-expanding frame 100 may be embedded within and/or disposed between adjacent layers of the proximal anchoring portion 334 of the occlusive membrane 330. In some embodiments, the distal anchoring portion 335 of the occlusive membrane 330 may be attached to the self-expanding frame 100, for example the distal anchoring portion 335 of the occlusive membrane 330 may be attached to a distal portion of the body of the self-expanding frame 100. In at least some embodiments, at least a portion of the self-expanding frame 100 may be embedded within and/or disposed between adjacent layers of the distal anchoring portion 335 of the occlusive membrane 330. For example, a portion of the body of the self-expanding frame 100 may be embedded within and/or disposed between adjacent layers of the distal anchoring portion 335 of the occlusive membrane 330. Other configurations are also contemplated.

In some embodiments, the proximal anchoring portion 334 of the occlusive membrane 330 may define a first length measured along the central longitudinal axis of the self-expanding frame 100. In some embodiments, the distal anchoring portion 335 of the occlusive membrane 330 may define a second length measured along the central longitudinal axis of the self-expanding frame 100. In some embodiments, the proximal suspended portion 332 of the occlusive membrane 330 may define a third length measured along the central longitudinal axis of the self-expanding frame 100. In some embodiments, the distal suspended portion 333 of the occlusive membrane 330 may define a fourth length measured along the central longitudinal axis of the self-expanding frame 100. In some embodiments, the third length of the proximal suspended portion 332 may be greater than the first length of the proximal anchoring portion 334. In some embodiments, the fourth length of the distal suspended portion 333 may be greater than the second length of the distal anchoring portion 335. In some embodiments, the first length of the proximal anchoring portion 334 and the second length of the distal anchoring portion 335 may be substantially equal. In some embodiments, the third length of the proximal suspended portion 332 and the fourth length of the distal suspended portion 333 may be substantially equal. Other configurations and relative relationships are also contemplated.

In some embodiments, the proximal suspended portion 332 of the occlusive membrane 330 may taper radially inward from the proximal anchoring portion 334 toward the narrowed waist 338. In some embodiments, the distal suspended portion 333 of the occlusive membrane 330 may taper radially inward from the distal anchoring portion 335 toward the narrowed waist 338. In some embodiments, the narrowed waist 338 may be configured to function as at least one vent configured to permit fluid to slowly pass through the narrowed waist 338 and/or the at least one vent to relieve pressure as thrombus and/or tissue overgrowth forms on and/or around the occlusive membrane 330 and/or the narrowed waist 338. Due to the design and/or arrangement of the occlusive membrane 330, fluid may slowly pass through the narrowed waist 338 in either the proximal direction or the distal direction to accommodate fluid flow regardless of direction of implantation and/or orientation of the vascular occlusion device within the lumen of the vessel 10.

Figure 5:
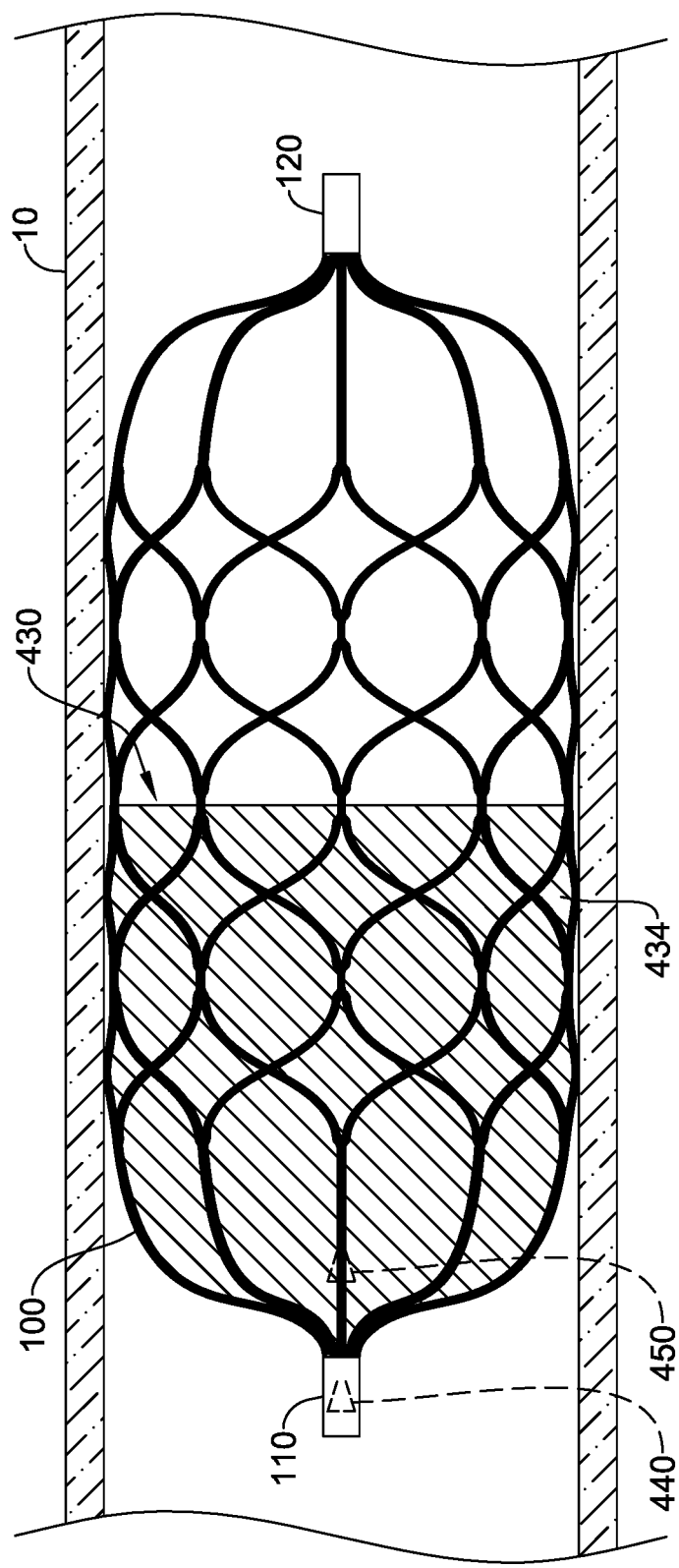
FIG. 5 illustrates aspects of an example vascular occlusion device.

In an alternative example illustrated in FIG. 5, in some embodiments, the vascular occlusion device may comprise the self-expanding frame 100 and an occlusive membrane 430 secured to the self-expanding frame 100. The occlusive membrane 430 may be substantially impermeable to fluid such that the occlusive membrane 430 is configured to substantially occlude and/or stop fluid flow through the lumen of the vessel 10. In some embodiments, the occlusive membrane 430 may be configured to completely occlude and/or stop fluid flow through the lumen of the vessel 10, initially and/or over time. Some suitable but non-limiting materials for the occlusive membrane 430, for example metallic materials, polymer materials, composite materials, etc., are described below.

In some embodiments, the occlusive membrane 430 may have an open end and a closed end, and the occlusive membrane may be secured to the self-expanding frame 100. In some embodiments, at least a portion of the occlusive membrane 430 may be configured to exert an additive radially outward force against the interior wall of the vessel 10 when fluid flows into the occlusive membrane 430 in the expanded configuration. In some embodiments, an anchoring portion 434 of the occlusive membrane 430 may be configured to exert an additive radially outward force against the interior wall of the vessel 10 when fluid flows into the occlusive membrane 430 in the expanded configuration. In some embodiments, at least a portion of the self-expanding frame 100 extending from the open end of the occlusive membrane 430 toward the closed end of the occlusive membrane 430, is embedded within the occlusive membrane 430. In at least some embodiments, the self-expanding frame 100, from the open end of the occlusive membrane 430 to the closed end of the occlusive membrane 430, may be embedded within and/or disposed between adjacent layers of the occlusive membrane 430. For example, a portion of the body of the self-expanding frame 100 and the first plurality of longitudinally-oriented struts may be embedded within and/or disposed between adjacent layers of the occlusive membrane 430. Other configurations are also contemplated.

In some embodiments, the occlusive membrane 430 may include a distal end attached to the distal hub 110 of the self-expanding frame 100. In some embodiments, the occlusive membrane 430 may taper radially inward from the body of the self-expanding frame 100 toward the distal hub 110 of the self-expanding frame 100. In some embodiments, the open end of the occlusive membrane 430 may be near and/or oriented towards the proximal hub 120 of the self-expanding frame 100 and the closed end of the occlusive membrane 430 may be near and/or oriented towards the distal hub 110 of the self-expanding frame 100. Other configurations are also contemplated.

In some embodiments, the vascular occlusion device may include at least one vent 440/450 proximate the closed end of the occlusive membrane 430, as shown in FIG. 5. In some embodiments, the at least one vent 440 may be formed within the distal hub 110 of the self-expanding frame 100. In some embodiments, the at least one vent 440 may include a plurality of cuts through the distal hub 110, the plurality of cuts being configured to permit the at least one vent 440 to open at a pre-defined pressure level. In one example, the plurality of cuts may form a flap configured to assume a normally closed position at a fluid pressure within the occlusive membrane 430 less than the pre-defined pressure level. Upon reaching and/or surpassing the pre-defined pressure level within the occlusive membrane 430, the flap may be configured to assume an open position thereby permitting fluid to pass through the at least one vent to relieve pressure as thrombus and/or tissue overgrowth forms on and/or around the occlusive membrane 430 and/or the at least one vent 440.

In some embodiments, the at least one vent 450 may be formed within the occlusive membrane 430 proximal of the closed end of the occlusive membrane 430, as shown in FIG. 5. In some embodiments, the at least one vent 450 may include a plurality of cuts through the occlusive membrane 430, the plurality of cuts being configured to permit the at least one vent 450 to open at a pre-defined pressure level. In one example, the plurality of cuts may form a flap configured to assume a normally closed position at a fluid pressure within the occlusive membrane 430 less than the pre-defined pressure level. Upon reaching and/or surpassing the pre-defined pressure level within the occlusive membrane 430, the flap may be configured to assume an open position thereby permitting fluid to pass through the at least one vent 450 to relieve pressure as thrombus and/or tissue overgrowth forms on and/or around the occlusive membrane 430 and/or the at least one vent 450.

Figure 6:
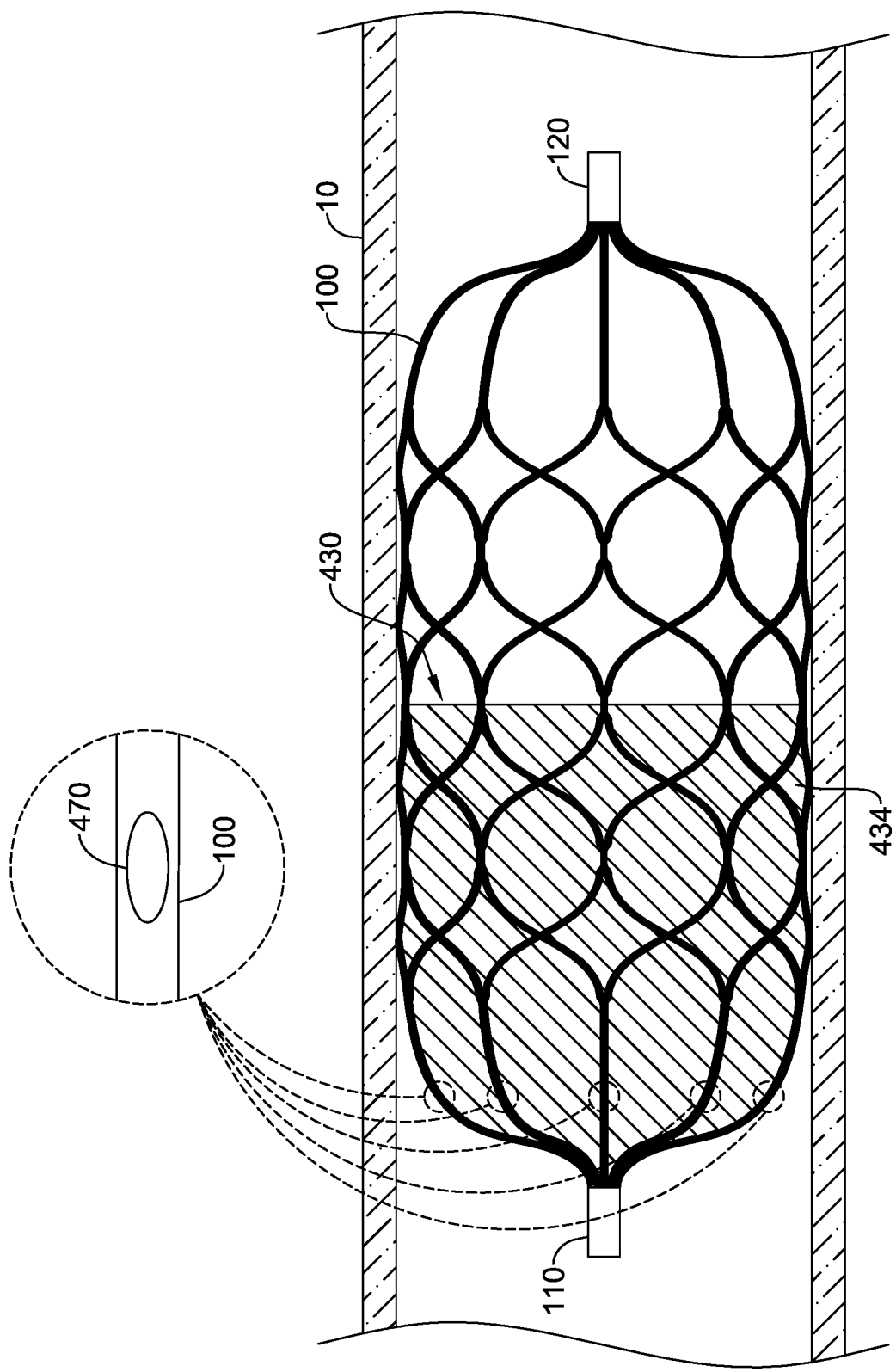
FIG. 6 illustrates aspects of an example vascular occlusion device.

In some embodiments, the vascular occlusion device may include at least one vent 470 formed within the self-expanding frame 100, as seen in FIG. 6. In some embodiments, the vascular occlusion device may include at least one vent 470 formed within the self-expanding frame 100 proximate the closed end of the occlusive membrane 430. In some embodiments, the vascular occlusion device may include at least one vent 470 formed within the self-expanding frame 100 proximal of the closed end of the occlusive membrane 430. In some embodiments, the vascular occlusion device may include at least one vent 470 formed within the self-expanding frame 100 distal of the open end of the occlusive membrane 430. In some embodiments, the vascular occlusion device may include at least one vent 470 formed within the self-expanding frame 100 at a location radially inward of a maximum outer extent of the self-expanding frame 100.

In some embodiments, the at least one vent 470 may be configured to permit fluid to slowly pass through the at least one vent 470 to relieve pressure as thrombus and/or tissue overgrowth forms on and/or around the occlusive membrane 430 and/or the at least one vent 470. In some embodiments, the at least one vent 470 may include at least one vent 470 formed in one or more of the first plurality of longitudinally-oriented struts of the self-expanding frame 100. In some embodiments, the at least one vent 470 may include at least one vent 470 formed in each of the first plurality of longitudinally-oriented struts of the self-expanding frame 100. In some embodiments, each of the first plurality of longitudinally-oriented struts of the self-expanding frame 100 may include one vent 470, two vents 470, three vents 470, or more. Similarly, in some embodiments, not every one of the first plurality of longitudinally-oriented struts of the self-expanding frame 100 may include at least one vent 470. For example, at least one vent 470 may be formed in every other (e.g., alternating) struts of the plurality of longitudinally-oriented struts of the self-expanding frame 100. In some embodiments, the at least one vent 470 may be disposed along the body of the self-expanding frame 100. In some embodiments, the at least one vent 470 may be disposed at a node or intersection of the plurality of interconnected struts and/or the lattice support structure in the body of the self-expanding frame 100. In some embodiments, the at least one vent 470 may have a fixed size and/or shape that does not change as the vascular occlusion device and/or the self-expanding frame 100 opens and/or expands. Other arrangements are also contemplated.

Figure 7:
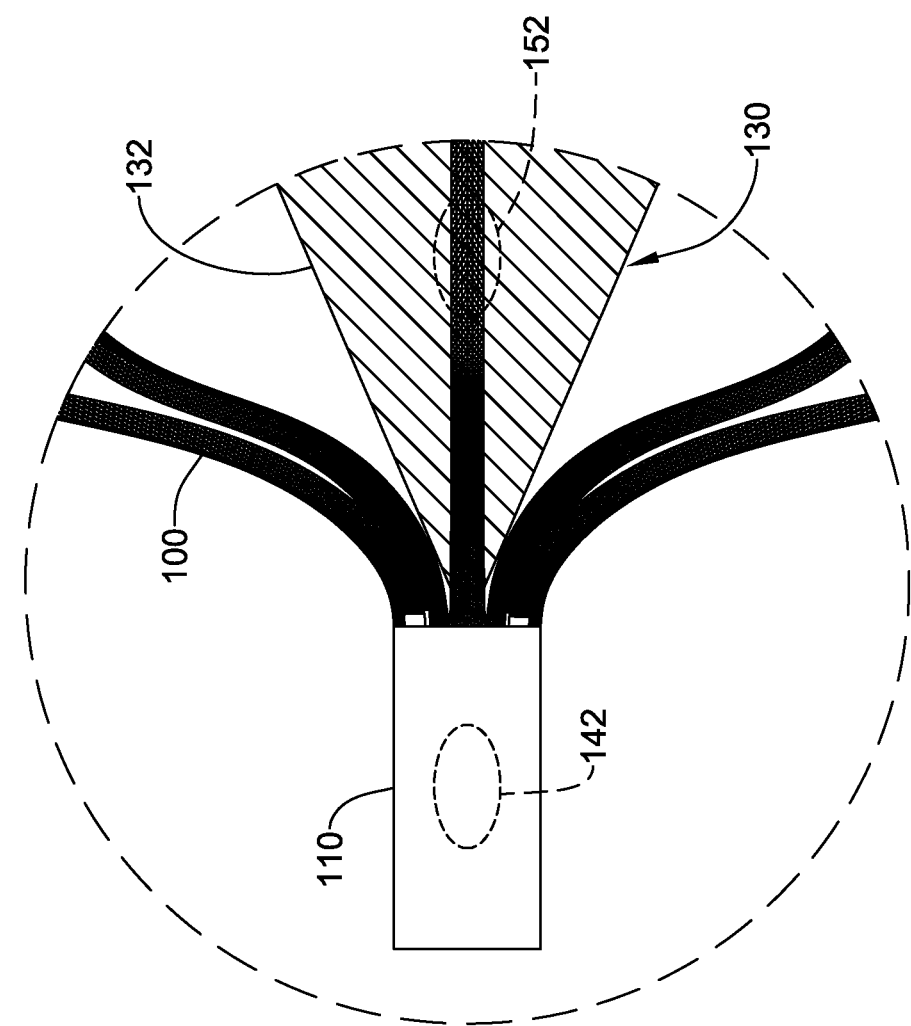
FIGS. 7-8 are detailed views illustrating alternative aspects of an example vascular occlusion device.

FIG. 7 illustrates alternative configurations for the at least one vent of any of the above embodiments. In some embodiments, the at least one vent formed in the distal hub 110 may be a hole or aperture 142 configured to permit fluid to slowly pass through the at least one vent and/or the hole or aperture 142 to relieve pressure as thrombus and/or tissue overgrowth forms on and/or around the occlusive membrane 130 and/or the at least one vent and/or the hole or aperture 142, as discussed above with respect to the at least one vent 140. In some embodiments, the at least one vent formed in the suspended portion 132 of the occlusive membrane 130 may be a hole or aperture 152 configured to permit fluid to slowly pass through the at least one vent and/or the hole or aperture 152 to relieve pressure as thrombus and/or tissue overgrowth forms on and/or around the occlusive membrane 130 and/or the at least one vent and/or the hole or aperture 152, as discussed above with respect to the at least one vent 150. In some embodiments, the hole or aperture 152 may have a fixed size and/or shape that does not change as the vascular occlusion device and/or the self-expanding frame 100 opens and/or expands. Other configurations, including combinations with other disclosed configurations, are also contemplated.

Figure 8:
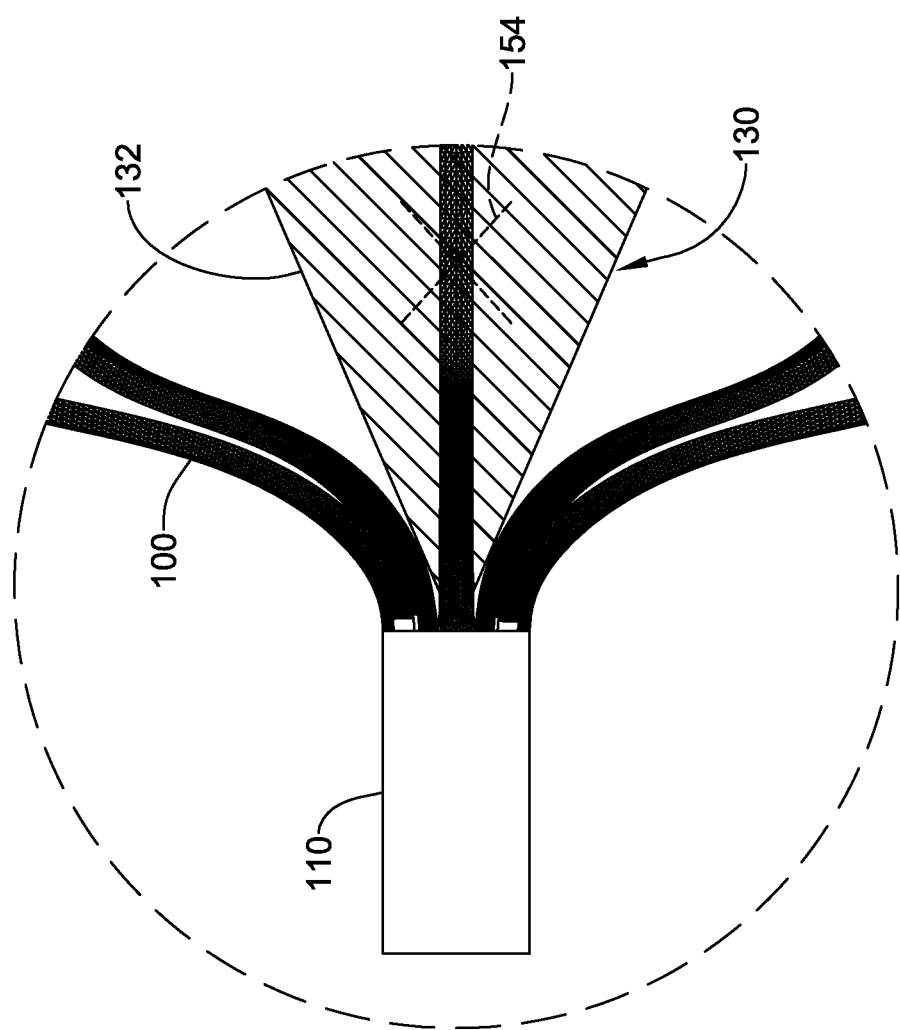

FIG. 8 illustrates an alternative configuration for the at least one vent of any of the above embodiments. In some embodiments, the at least one vent may be formed within the suspended portion 132 of the occlusive membrane 130 proximal of the closed end of the occlusive membrane 130. In some embodiments, the at least one vent may include a plurality of cuts and/or slits 154 through the occlusive membrane 130, the plurality of cuts and/or slits 154 being configured to permit the at least one vent to open at a pre-defined pressure level. In one example, the plurality of cuts or slits 154 may form at least one flap configured to assume a normally closed position at a fluid pressure within the occlusive membrane 130 less than the pre-defined pressure level. Upon reaching and/or surpassing the pre-defined pressure level within the occlusive membrane 130, the at least one flap may be configured to assume an open position thereby permitting fluid to pass through the at least one vent to relieve pressure as thrombus and/or tissue overgrowth forms on and/or around the occlusive membrane 130 and/or the at least one vent, as discussed above with respect to the at least one vent 150. Other configurations, including combinations with other disclosed configurations, are also contemplated.

In any of the above disclosed and/or contemplated configurations, a position of the at least one vent 150/152/154/450/470 may vary along the length of the occlusive membrane 130 and/or the self-expanding frame 100. Similarly, the position of the at least one vent 150/152/154/450/470 may vary with respect to a diameter of the occlusive membrane 130 and/or the self-expanding frame 100. The vascular occlusion device may be configured, designed, intended, and/or rated for use in a vessel 10 having a vessel inner diameter V. In some embodiments, the at least one vent 150/152/154/450/470 may be positioned according to the vessel inner diameter V of the vessel 10 in which the vascular occlusion device is configured, designed, intended, and/or rated for use.

For example, a vascular occlusion device may have a maximum outer extent of about 8 mm (e.g., about 4 mm about a central longitudinal axis of the vascular occlusion device), and may be configured, designed, intended, and/or rated for use in a vessel 10 having a vessel inner diameter V of about 3-6 mm. In some applications, the total radially outward force (the radially outward force exerted by the self-expanding frame 100 combined with the additive radially outward force exerted by the anchoring portion 134/234/334/335/434 of the occlusive membrane 130/230/330/430) exerted on the interior wall of the vessel 10 may cause the vessel 10 to stretch. In some embodiments, the vessel 10 may flex, stretch, or expand due to vessel spasm and/or fluid pressure increases during initial placement of the vascular occlusion device. As such, a vascular occlusion device having a maximum outer extent that is greater than the vessel inner diameter V is usually desired for proper anchoring and to prevent of migration of the vascular occlusion device.

In some embodiments and/or uses, it may be desirable to permit the vascular occlusion device to vent and/or relieve pressure from within the occlusive membrane 130/230/330/430, for example during a recapture operation and/or until the vascular occlusion device is fully seated/anchored in the vessel 10. In some embodiments, as the vascular occlusion device approaches its maximum outer extent, pressure build-up within the occlusive membrane 130/230/330/430 may reduce and/or overcome the additive radially outward force being exerted against the interior wall of the vessel 10. One example of this may be during initial deployment of the vascular occlusion device, before the vascular occlusion device has been able to fully seat/anchor in the vessel 10. One example way of addressing this phenomenon is with the positioning of the at least one vent 150/152/154/450/470. In some embodiments, the at least one vent 150/152/154/450/470 may be positioned to permit the release of fluid and/or pressure from within the occlusive membrane 130/230/330/430 as the vascular occlusion device expands to near the maximum outer extent of the vascular occlusion device, which may help prevent unintended and/or undesired migration of the vascular occlusion device (for example, due to fluid pressure overcoming available anchoring forces).

In the example above of a vascular occlusion device having a maximum outer extent of about 8 mm configured, designed, intended, and/or rated for use in a vessel 10 having a vessel inner diameter V of about 3-6 mm, the at least one vent 150/152/154/450/470 may be positioned at about 5.5 mm diameter of the self-expanding frame 100 and/or the occlusive membrane 130/230/330/430 (e.g., about 2.75 mm about the central longitudinal axis of the vascular occlusion device). Other dimensions, positions, variations, and/or combinations are also contemplated.

In the stated example, whenever the vascular occlusion device opens to a maximum outer extent greater than about 5.5 mm, the at least one vent 150/152/154/450/470 may be unobstructed by the interior wall of the vessel 10 and/or "open", to permit the release of fluid and/or pressure from within the occlusive membrane 130/230/330/430. Over time, the at least one vent 150/152/154/450/470 may become occluded as thrombus forms and completely blocks fluid flow through the lumen of the vessel 10, but during initial placement and/or recapture, dynamic pressure relief may be desirable.

In the same stated example, if the vessel inner diameter V is less than about 5.5 mm (e.g., about 5 mm, about 4 mm, etc.), the at least one vent 150/152/154/450/470 may be in apposition and/or full contact with the interior wall of the vessel 10, thereby blocking, plugging, or "closing" the at least one vent 150/152/154/450/470 and preventing the flow of fluid through the at least one vent 150/152/154/450/470. In this way, the at least one vent 150/152/154/450/470 may provide temporary pressure relief and/or fluid release during initial expansion of the vascular occlusion device and/or during recapture of the vascular occlusion device.

In some embodiments, the vascular occlusion device may include an atraumatic tip on the proximal hub 120 and/or the distal hub 110. For example, the atraumatic tip may face distally with respect to the self-expanding frame 100 and/or may define a distalmost end of the vascular occlusion device and/or the self-expanding frame 100, and/or the atraumatic tip may face proximally with respect to the self-expanding frame 100 and/or may define a proximalmost end of the vascular occlusion device and/or the self-expanding frame 100. In some embodiments, the atraumatic tip may be formed with an adhesive substance, a bonding agent, a weld, or another suitable means. Some suitable but non-limiting materials for the atraumatic tip, for example metallic materials, polymer materials, composite materials, etc., are described below.

The materials that can be used for the various components of the vascular occlusion device, the self-expanding frame 100, the occlusive membrane 130/230/330/430, etc. (and/or other systems disclosed herein) and the various elements thereof disclosed herein may include those commonly associated with medical devices. For simplicity purposes, the following discussion makes reference to the vascular occlusion device, the self-expanding frame 100, the occlusive membrane 130/230/330/430, etc. However, this is not intended to limit the devices and methods described herein, as the discussion may be applied to other elements, members, components, or devices disclosed herein, such as, but not limited to, the vascular occlusion device, the self-expanding frame 100, the occlusive membrane 130/230/330/430, etc. and/or elements or components thereof.

In some embodiments, the vascular occlusion device, the self-expanding frame 100, the occlusive membrane 130/230/330/430, etc., and/or components thereof (such as, but not limited to, the body, the first plurality of longitudinally-oriented struts, the second plurality of longitudinally-oriented struts, the distal hub 110, the proximal hub 120, the suspended portion 132/232/332/333, the anchoring portion 134/234/334/335/434, the atraumatic tip, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the vascular occlusion device, the self-expanding frame 100, the occlusive membrane 130/230/330/430, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the vascular occlusion device, the self-expanding frame 100, the occlusive membrane 130/230/330/430, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the vascular occlusion device, the self-expanding frame 100, the occlusive membrane 130/230/330/430, etc. to achieve the same result.

In some embodiments, a degree of Magnetic Resonance Imaging (MRI) compatibility is imparted into the vascular occlusion device, the self-expanding frame 100, the occlusive membrane 130/230/330/430, etc. For example, the vascular occlusion device, the self-expanding frame 100, the occlusive membrane 130/230/330/430, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The vascular occlusion device, the self-expanding frame 100, the occlusive membrane 130/230/330/430, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the vascular occlusion device, the self-expanding frame 100, the occlusive membrane 130/230/330/430, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the vascular occlusion device, the self-expanding frame 100, the occlusive membrane 130/230/330/430, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the vascular occlusion device, the self-expanding frame 100, the occlusive membrane 130/230/330/430, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the vascular occlusion device, the self-expanding frame 100, the occlusive membrane 130/230/330/430, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A vascular occlusion device for deployment within a lumen of a vessel, comprising:
   a self-expanding frame configured to shift between a collapsed configuration and an expanded configuration, the self-expanding frame defining a perimeter of an interior space disposed within the self-expanding frame,
   wherein the self-expanding frame is configured to exert a radially outward force against an interior wall of the vessel in the expanded configuration; and
   an occlusive membrane secured to the self-expanding frame,
   wherein the occlusive membrane includes a suspended portion disposed within the self-expanding frame and spaced apart from the perimeter of the interior space,
   wherein the occlusive membrane includes a distal end attached directly to a distal hub of the self-expanding frame,
   wherein the occlusive membrane includes an anchoring portion configured to exert an additive radially outward force against the interior wall of the vessel when fluid flows into the occlusive membrane in the expanded configuration.

2. The vascular occlusion device of claim 1, wherein the anchoring portion is attached to the self-expanding frame.

3. The vascular occlusion device of claim 1, wherein the self-expanding frame is embedded within the anchoring portion.

4. The vascular occlusion device of claim 1, wherein the anchoring portion defines a length measured along a central longitudinal axis of self-expanding frame, the suspended portion defines a length measured along the central longitudinal axis, and the length of the suspended portion is greater than the length of the anchoring portion.

5. The vascular occlusion device of claim 1, wherein the suspended portion of the occlusive membrane tapers radially inward toward a distal hub of the self-expanding frame.

6. The vascular occlusion device of claim 1, wherein the occlusive membrane includes an open end oriented towards a proximal hub of the self-expanding frame and a closed end oriented towards a distal hub of the self-expanding frame.

7. The vascular occlusion device of claim 6, further including at least one vent proximate the closed end of the occlusive membrane.

8. The vascular occlusion device of claim 7, wherein the at least one vent includes a plurality of cuts through the occlusive membrane, the plurality of cuts being configured to permit the at least one vent to open at a pre-defined pressure level.

9. The vascular occlusion device of claim 6, further including at least one vent formed within the suspended portion of the occlusive membrane proximal of the closed end.

10. The vascular occlusion device of claim 1, wherein the occlusive membrane includes at least one flap configured to assume a normally open position at a first fluid pressure within the occlusive membrane and configured to assume an closed position at a second fluid pressure less than the first fluid pressure within the occlusive membrane.

11. A vascular occlusion device for deployment within a lumen of a vessel, comprising:
a self-expanding frame configured to shift between a collapsed configuration and an expanded configuration, wherein the self-expanding frame is configured to exert a radially outward force against an interior wall of the vessel in the expanded configuration; and
an occlusive membrane having an open end and a closed end, the occlusive membrane being secured to the self-expanding frame;
wherein the occlusive membrane includes an anchoring portion extending longitudinally along the self-expanding frame, the anchoring portion configured to exert an additive radially outward force against the interior wall of the vessel when fluid flows into the open end of the occlusive membrane in the expanded configuration;
wherein at least a portion of the self-expanding frame extending from the open end of the occlusive membrane toward the closed end of the occlusive membrane, is embedded within the occlusive membrane;
wherein at least one vent is formed within one or more struts of the self-expanding frame.

12. The vascular occlusion device of claim 11, wherein the at least one vent is formed within the self-expanding frame at a location radially inward of a maximum outer extent of the self-expanding frame.

13. The vascular occlusion device of claim 11, wherein each of the at least one vent may be disposed at a node within a body of the self-expanding frame.

14. The vascular occlusion device of claim 11, wherein the occlusive membrane includes at least one flap configured to assume a normally open position at a first fluid pressure within the occlusive membrane and configured to assume an closed position at a second fluid pressure less than the first fluid pressure within the occlusive membrane.

15. A vascular occlusion device for deployment within a lumen of a vessel, comprising:
a self-expanding frame configured to shift between a collapsed configuration and an expanded configuration, the self-expanding frame defining a perimeter of an interior space disposed within the self-expanding frame; and
an occlusive membrane secured to the self-expanding frame;
wherein the occlusive membrane includes a suspended portion disposed within the self-expanding frame and spaced apart from the perimeter of the interior space;
wherein the self-expanding frame is configured to exert a radially outward force against an interior wall of the vessel in the expanded configuration;
wherein the suspended portion includes a proximal suspended portion opening toward a proximal hub of the self-expanding frame and a distal suspended portion opening toward a distal hub of the self-expanding frame, the proximal suspended portion and the distal suspended portion being joined together at a narrowed waist of the occlusive membrane,
wherein the proximal suspended portion includes a proximal anchoring portion extending longitudinally along the self-expanding frame, the anchoring portion configured to exert an additive radially outward force against the interior wall of the vessel when fluid flows into the occlusive membrane in a distal direction in the expanded configuration.

16. The vascular occlusion device of claim 15, wherein the proximal anchoring portion is attached to the self-expanding frame.

17. The vascular occlusion device of claim 15, wherein the distal suspended portion includes a distal anchoring portion configured to exert an additive radially outward force against the interior wall of the vessel when fluid flows into the occlusive membrane in a proximal direction in the expanded configuration.

18. The vascular occlusion device of claim 17, wherein the distal anchoring portion is attached to the self-expanding frame.

19. The vascular occlusion device of claim 15, wherein the occlusive membrane includes at least one flap configured to assume a normally open position at a first fluid pressure within the occlusive membrane and configured to assume an closed position at a second fluid pressure less than the first fluid pressure within the occlusive membrane.

* * * * *